US012559489B2

(12) United States Patent
Choi

(10) Patent No.: US 12,559,489 B2
(45) Date of Patent: Feb. 24, 2026

(54) ANTAGONISTIC SMALL MOLECULE COMPOUND HAVING TOLL-LIKE RECEPTOR 7/9 INHIBITORY FUNCTION

(71) Applicant: AJOU UNIVERSITY INDUSTRY-ACADEMIC COOPERATION FOUNDATION, Suwon-si (KR)

(72) Inventor: Sangdun Choi, Suwon-si (KR)

(73) Assignee: AJOU UNIVERSITY INDUSTRY-ACADEMIC COOPERATION FOUNDATION, Suwon-si (KR)

(*) Notice: Subject to any disclaimer, the term of this patent is extended or adjusted under 35 U.S.C. 154(b) by 616 days.

(21) Appl. No.: 17/923,061

(22) PCT Filed: May 4, 2021

(86) PCT No.: PCT/KR2021/005624
§ 371 (c)(1),
(2) Date: Nov. 3, 2022

(87) PCT Pub. No.: WO2021/225365
PCT Pub. Date: Nov. 11, 2021

(65) Prior Publication Data

US 2023/0339935 A1 Oct. 26, 2023

(30) Foreign Application Priority Data

May 4, 2020 (KR) ........................ 10-2020-0053335

(51) Int. Cl.
*C07D 471/04* (2006.01)

(52) U.S. Cl.
CPC .................................. *C07D 471/04* (2013.01)

(58) Field of Classification Search
CPC ....... A61K 27/00; A61K 31/437; A61P 29/00; C07D 471/04
See application file for complete search history.

(56) References Cited

U.S. PATENT DOCUMENTS

| | | | |
|---|---|---|---|
| 5,124,335 A | 6/1992 | Patchett et al. | |
| 7,504,509 B2 * | 3/2009 | Ibrahim | C07D 471/04 546/113 |
| 2009/0143352 A1 | 6/2009 | Arnold et al. | |

FOREIGN PATENT DOCUMENTS

| | | | |
|---|---|---|---|
| CN | 106467481 A * | 3/2017 | C07D 209/12 |
| KR | 10-1746199 B1 | 6/2017 | |
| WO | 2007/002325 A1 | 1/2007 | |
| WO | 2018/134254 A1 | 7/2018 | |
| WO | 2020/016243 A1 | 1/2020 | |

OTHER PUBLICATIONS

Sawada, Chem. Pharm. Bull. 49(7) 799-813 (2001). (Year: 2001).*
CN106467481A, machine translation. (Year: 2017).*
Zhihong Huang et al., "Discovery of 5-(3,4-Difluorophenyl)-3-(pyrazol-4-yl)-7-azaindole (GNF3809) for β-Cell Survival in Type 1 Diabetes", ACS Omega, 2019, pp. 3571-3581, vol. 4, No. 2.
International Search Report for PCT/KR2021/005624, dated Aug. 6, 2021.
The Extended European Search Report dated May 21, 2024, issued in European Application No. 21800188.1.
Anjali Jaiswal et al., "Synthesis of 3-acylindoles via copper-mediated oxidative decarbethoxylation of ethyl arylacetates", Organic & Biomolecular Chemistry, 2020, vol. 18, pp. 1623-1628 (6 pages).
Kristine K. Deibler et al., "A Chemical Probe Strategy for Interrogating Inhibitor Selectivity Across the MEK Kinase Family", ACS Chemical Biology, 2017, vol. 12, pp. 1245-1256 (12 pages).
Demaria et al., "TLR8 deficiency leads to autoimmunity in mice", The Journal of Clinical Investigation, 2010, vol. 120, No. 10, pp. 3651-3662 (12 pages total).
Heil et al., "Species-Specific Recognition of Single-Stranded RNA via Toll-like Receptor 7 and 8", Science, 2004, vol. 303, pp. 1526-1529 (4 pages total).
Diebold et al., Innate Antiviral Response by Means of TLR7-Mediated Recognition of Single-Stranded RNA, Science, 2004, vol. 303, pp. 1529-1531 (4 pages total).
Hemmi et al., "Small anti-viral compounds activate immune cells via the TLR7 MyD88-dependent signaling pathway", Nature Immunology, 2002, vol. 3, No. 2, pp. 196-200 (5 pages total).
Krieg et al., "Toll-like receptors 7, 8, and 9: linking innate immunity to autoimmunity", Immunological Reviews, 2007, vol. 220, pp. 251-269 (19 pages total).
Hemmi et al., "A Toll-like receptor recognizes bacterial DNA", Letters to Nature, 2000, vol. 408, pp. 740-745 (6 pages total).
Poltorak et al., "Defective LPS Signaling in C3H/HeJ and C57BL/10ScCr Mice: Mutations in Tlr4 Gene", Science, 1998, vol. 282, pp. 2085-2088 (5 pages total).
Takeuchi et al., "Discrimination of bacterial lipoproteins by Toll-like receptor 6", International Immunology, 2001, vol. 13, No. 7, pp. 933-940 (8 pages total).
Takeuchi et al., "Cutting Edge: Role of Toll-Like Receptor 1 in Mediating Immune response to Microbial Lipoproteins", The Journal of Immunology, 2002, pp. 10-14, (6 pages total).
Terhorst et al., Dynamics and Transcriptomics of Skin Dendritic Cells and Macrophages in an Imiquimod-Induced, Biphasic Mouse Model of Psoriasis, The Journal of Immunology, 2015, pp. 1-9 (10 pages total).
Vincent et al., "The BAFF/APRIL system in SLE pathogenesis", Nat. Rev. Rheumatol, 2014, vol. 10, pp. 365-373, (9 pages total).
Korean Patent Office, Communication issued Jul. 18, 2025 in copending Application No. 10-2020-0053335.

* cited by examiner

*Primary Examiner* — Layla D Berry
(74) *Attorney, Agent, or Firm* — Sughrue Mion, PLLC

(57) ABSTRACT

An antagonistic small molecule compound having a Toll-like receptor (TLR) 7/9 inhibitory function, a method for producing the same, and a composition containing the compound are disclosed. The novel small molecule compound has a function of inhibiting a TLR7/9 signaling path. The novel compound not only blocks secretion of TMF-α induced by CpG-ODN (TLR9 agonist) or IMQ (TLR7 agonist) but also inhibits generation of inflammatory cytokines and, thus, is useful for prevention or treatment of TLR7/9-related autoimmune diseases and inflammatory diseases including systemic lupus erythematosus and psoriasis, in particular.

6 Claims, 5 Drawing Sheets

FIG. 1A
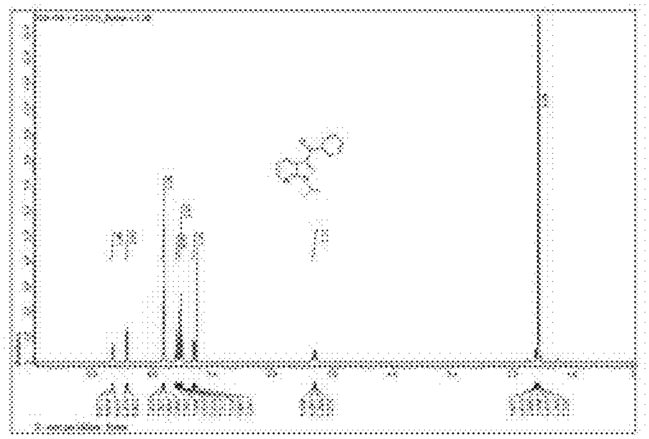
FIG. 1B
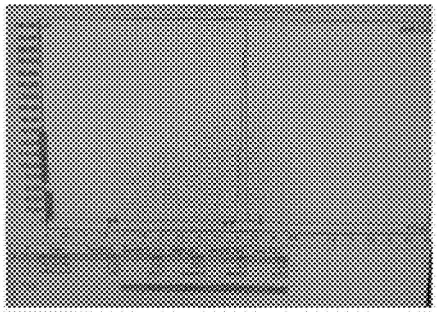
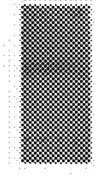
FIG. 1C
FIG. 2A
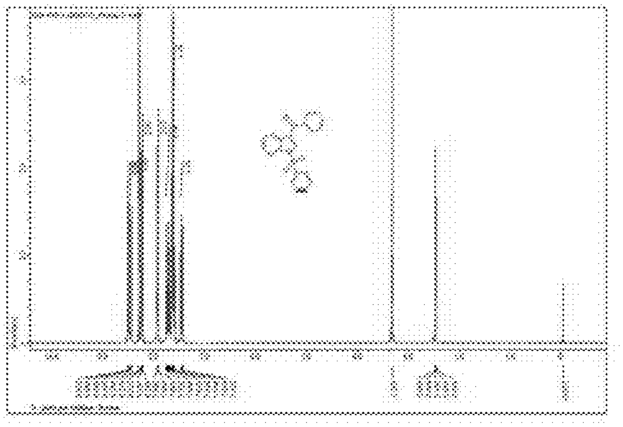
FIG. 2B
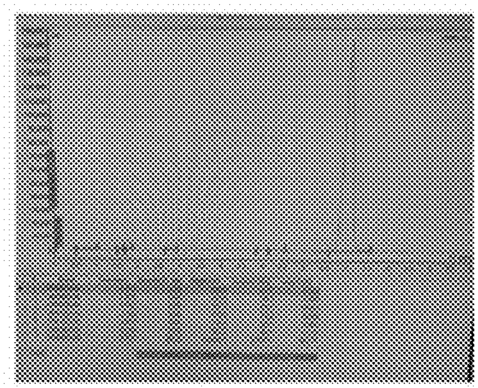
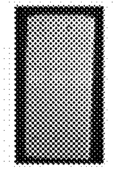
FIG. 2C FIG. 3A
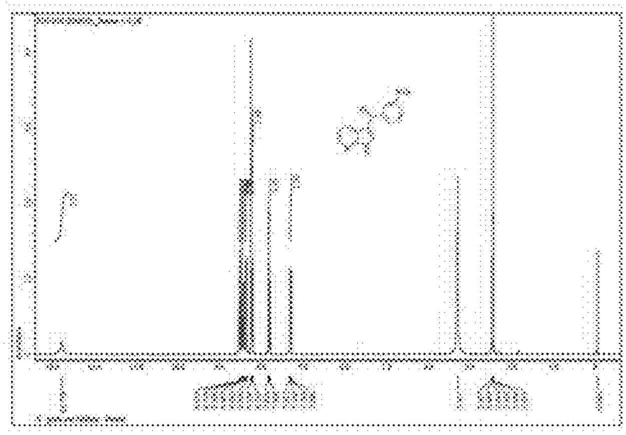
FIG. 3B
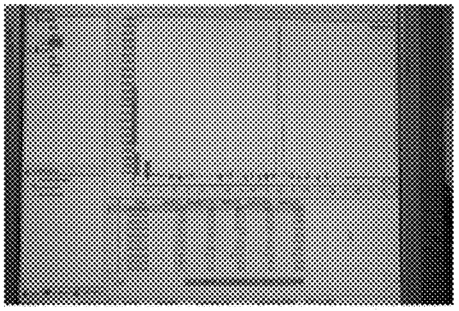
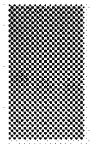
FIG. 3C
FIG. 4A
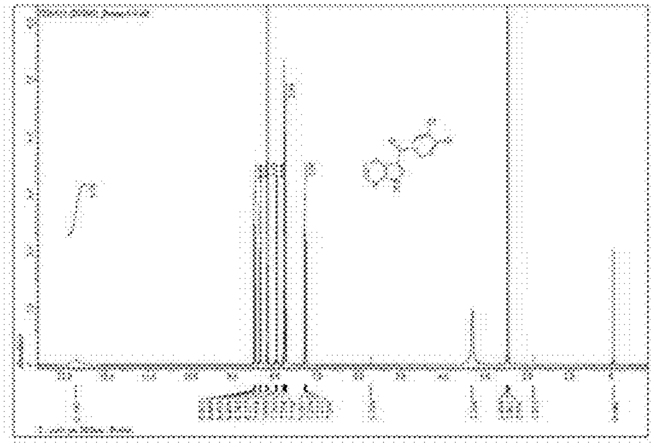
FIG. 4B
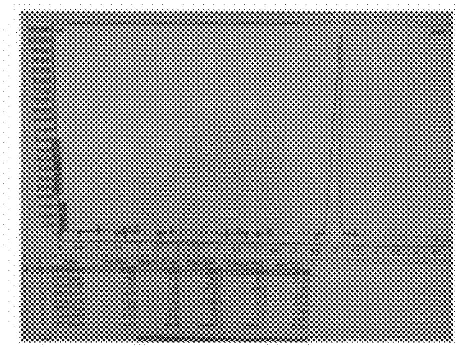
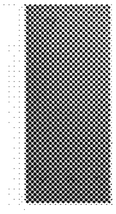
FIG. 4C FIG. 5A
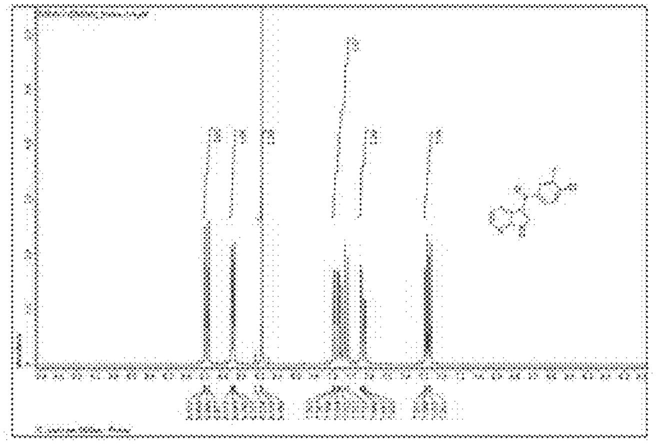
FIG. 5B
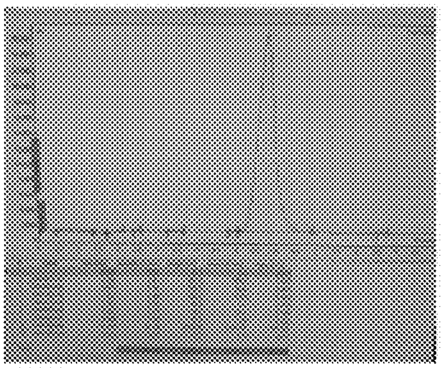
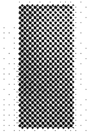
FIG. 5C
FIG. 6A
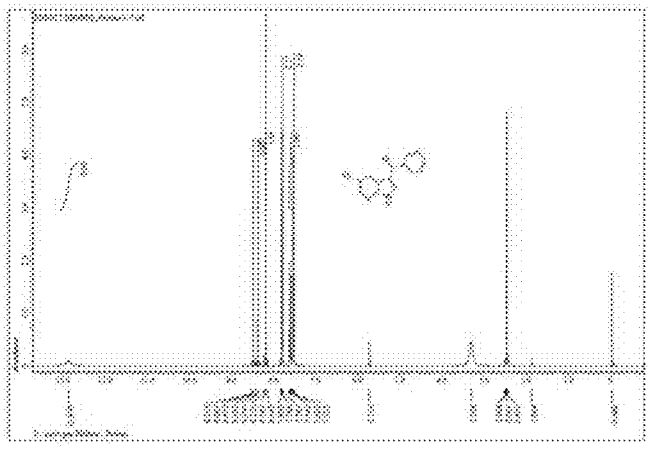
FIG. 6B
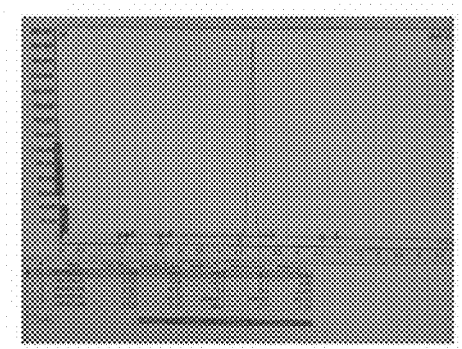
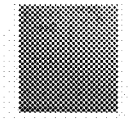
FIG. 6C

ANTAGONISTIC SMALL MOLECULE COMPOUND HAVING TOLL-LIKE RECEPTOR 7/9 INHIBITORY FUNCTION

CROSS REFERENCE TO RELATED APPLICATIONS

This application is a National Stage of International Application No. PCT/KR2021/005624 filed May 4, 2021, claiming priority based on Korean Patent Application No. 10-2020-0053335 filed May 4, 2020.

TECHNICAL FIELD

The present invention relates to an antagonistic small molecule compound having an inhibitory activity against toll-like receptor (TLR) 7/9, and more particularly, to a novel small-molecule compound inhibiting the signaling pathway of toll-like receptor 7/9, a method of preparing the same, and a composition for preventing or treating an autoimmune disease or an inflammatory disease containing the same.

BACKGROUND ART

Innate (or congenital) immunity is the first defense line against bacterial infection in the mammalian immune system and is activated when pattern recognition receptors such as toll-like receptors (TLRs) recognize pathogen-associated molecular patterns (PAMPs) or danger-associated molecular patterns (DAMPs). Examples include triacyl lipoprotein (e.g. $Pam_3CSK_4$) recognized by TLR1/2 (Takeuchi, O. et al., *J. Immunol.* 169: 10-14 (2002)), diacyl lipoprotein (e.g. Pam2CSK4) recognized by TLR2/6 (Takeuchi, O. et al., *Int. Immunol.* 13: 933-940 (2001)), lipopolysaccharide (LPS) recognized by TLR4 (Poltorak, A. et al., *Science* 282: 2085-2088 (1998)), bacterial flagellin recognized by TLR5 (Poltorak, A. et al. *Science* 282: 2085-2088 (1998), viral double-stranded RNA (dsRNA) recognized by TLR3 (Poltorak, A. et al. al., *Science* 282: 2085-2088 (1998)), viral single-stranded RNA (ssRNA) recognized by TLR7 and TLR8 (Diebold, S. S. et al., *Science* 303: 1529-1531 (2004); Heil, F. et al., Science 303: 1526-1529 (2004)), unmethylated CpG-containing oligodeoxynucleotides (ODN) recognized by TLR9 (Hemmi, H. et al. *Nature* 408: 740-745 (2000)) and the like.

TLRs play a key role in the innate immune response, and are classified into extracellular TLRs acting on the plasma membrane, including TLR1, TLR2, TLR4, TRL5, TLR6 and TLR11, and intracellular TLRs acting in cells such as endosomes, including TLR3, TLR7, TLR8, and TLR9. Structurally, TLRs have a leucine-rich repeat (LRR) site recognized by a ligand or accessory molecule at the N-terminus of the extracellular domain, and have a toll/interleukin 1 receptor (TIR) domain that delivers a signal to the C-terminus of the intracellular part.

In particular, TLR7, TLR8, TLR9, and TLR3 detect exogenous single-stranded RNA (ssRNA), double-stranded RNA (dsRNA) and CpG DNA, which are exposed to endosomes from extracellular invading pathogens, or recognize, as ligands, endogenous ssRNA or DNA fragments exposed from tissue damaged by necrosis or apoptosis in tissue due to an abnormal response, thereby amplifying inflammatory cytokines through signaling processes. In general, TLR7 and TLR8 recognize ssRNA from influenza or damaged cells, while TLR9 detects CpG DNA fragments generated from the genome of bacteria and viruses or damaged tissue, and TLR3 recognizes dsRNA, which is an intermediate product of viral proliferation, thereby activating the innate immune response. Research on the use of TLR as a target for treatment of the immune-associated diseases is being actively conducted worldwide due to the known roles of TLR.

In MyD88 (myeloid differentiation primary response 88)-dependent signaling of TLR7/8/9, a dimer is formed with the corresponding ligand, and the TIR domain of TLR binds to the TIR domain of MyD88 to form a complex, so the signaling pathway is activated (Hemmi, H. et al., *Nat. Immunol.* 3, 196-200, (2002)). The activated TLR signal induces activation of NF-κB, migration thereof to the nucleus, and activation of MAPK, and expresses interferon α (IFNα) and IFN-inducible genes. The activation of NFα, κB and MAPK causes secretion of inflammatory cytokines such as TNFα, IL-1β (interleukin 1β) and IL-6. The MyD88-independent signaling process of TLR3 is initiated by binding between the TIR domain of TLR3 and the TIR domain of TRIF (TIR domain-containing adapter-inducing interferon-β), and type 1 interferon is secreted due to the activation of the interferon regulatory factor (IRF). In addition, TLR activity produces oxidative stressors such as NO and ROS in macrophages.

The TLRs (TLRs 3, 7, 8, and 9) in the endosome membrane play an important role in protecting hosts from various viral and bacterial infections. In particular, the expression of TLRs 7, 8, and 9 is essential for sustained defense against pathogenic components or self-antigens released from damaged or stressed tissue/cells (Demaria, O. et al., *J. Clin. Invest.* 120: 3651-3662 (2010)). Malfunctions of these nucleic-acid-sensing TLRs have been associated with several autoimmune pathologies such as psoriasis and systemic lupus erythematosus (SLE) (Vincent, FB et al., *Nat. Rev. Rheumatol.* 10: 365-373 (2014)). However, the etiology of these diseases remains unclear (Krieg, A. M. & Vollmer, J., *Immunol. Rev.* 220: 251-269 (2007); Terhorst, D. et al., *J. Immunol.* 195: 4953-4961 (2015)). Thus, there is increasing need for the development of novel antagonists that inhibit the progression of endosomal TLR-mediated diseases.

As described above, TLR may serve as a target for treatment of various diseases such as autoimmune diseases, inflammatory diseases, and cancer, and thus research has been actively conducted on substances targeting TLR and medical compositions for treating TLR-associated diseases.

Accordingly, as a result of intensive efforts to develop TLR-targeting substances and medical compositions for treating TLR-related diseases, the present inventors found that novel compounds including compounds defined as TAC5 (TLR antagonistic compound 5)-050 to TAC5-055 inhibit the secretion of cytokines by inhibiting the TLR signaling pathway induced by TLR7 or TLR9 activation, and completed the present invention based on this finding.

The information disclosed in this Background section is provided only for enhancement of understanding of the background of the present invention, and therefore it may not include information that forms the prior art that is already obvious to those skilled in the art.

SUMMARY OF THE INVENTION

It is one object of the present invention to provide an antagonistic small-molecule compound having a function of inhibiting toll-like receptors (TLRs) 7 and 9 and TLR7 and TLR9 inhibitors containing the same.

It is another object of the present invention to provide a pharmaceutical composition for preventing or treating an autoimmune disease or an inflammatory disease containing the compound.

It is another object of the present invention to provide a method for preventing or treating an autoimmune disease or inflammatory disease using the compound, the use of the compound for the prevention or treatment of an autoimmune disease or inflammatory disease, and the use of the compound for the preparation of a drug for preventing or treating an autoimmune disease or inflammatory disease.

In accordance with one aspect of the present invention, the above and other objects can be accomplished by the provision of a compound represented by the following Formula 1 or a pharmaceutically acceptable salt thereof:

[Formula 1]

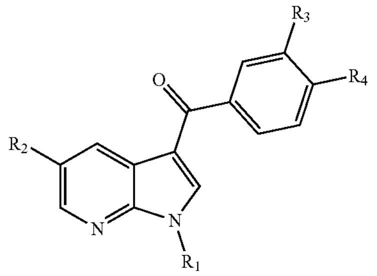

wherein $R_1$ to $R_4$ are the same as or different from each other, and are each independently a hydrogen atom, a halogen atom, straight- or branched-chain alkyl, amino, nitrile, nitro, nitroso, hydroxy, cycloalkyl, haloalkyl, allyl, alkoxy, alkylcarbonyl, cycloalkylcarbonyl, arylcarbonyl, alkylarylcarbonyl, alkoxycarbonyl, cycloalkoxy, aryl, heteroaryl, heterocycloalkyl, aryloxy, alkoxyheteroaryl, benzenesulfonyl, benzylsulfonyl, heteroaryloxyalkyl, alkylheteroaryl, alkylaryl, arylalkyl, alkylheteroaryl, alkylester, alkylamide or acryl, wherein the alkyl or the alkoxy is $C_{1-30}$ alkyl or alkoxy, the cycloalkyl is $C_{3-30}$ cycloalkyl, the allyl is $C_{2-30}$ allyl, the aryl is $C_{6-30}$ aryl, and the heteroaryl and the heterocycloalkyl contain a heteroatom selected from fluorine, oxygen, sulfur, and nitrogen.

In accordance with another aspect of the present invention, provided is a method of preparing a compound represented by Formula 1-1 below.

[Formula 1-1]

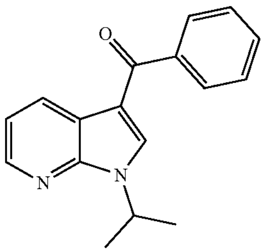

In accordance with another aspect of the present invention, provided is a method of preparing a compound represented by Formula 1-2 below.

[Formula 1-2]

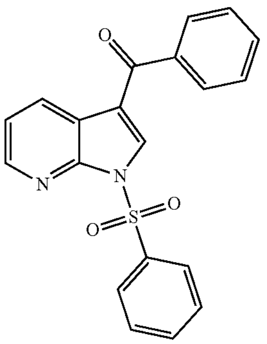

In accordance with another aspect of the present invention, provided are a method for preventing or treating an autoimmune disease or inflammatory disease using the compound of Formula 1, the use of the compound for the prevention or treatment of an autoimmune disease or inflammatory disease, and the use of the compound for the preparation of a drug for preventing or treating an autoimmune disease or inflammatory disease.

DESCRIPTION OF DRAWINGS

FIG. 1A-1C show NMR data, HPLC data, and TLC data of prepared TAC5-050.

FIG. 2A-2C show NMR data, HPLC data, and TLC data of prepared TAC5-051.

FIG. 3A-3C shows NMR data, HPLC data, and TLC data of prepared TAC5-052.

FIG. 4A-4C show NMR data, HPLC data, and TLC data of prepared TAC5-053.

FIG. 5A-5C show NMR data, HPLC data, and TLC data of prepared TAC5-054.

FIG. 6A-6B show NMR data, HPLC data, and TLC data of prepared TAC5-055.

DETAILED DESCRIPTION AND PREFERRED EMBODIMENTS OF THE INVENTION

Figure 7A:
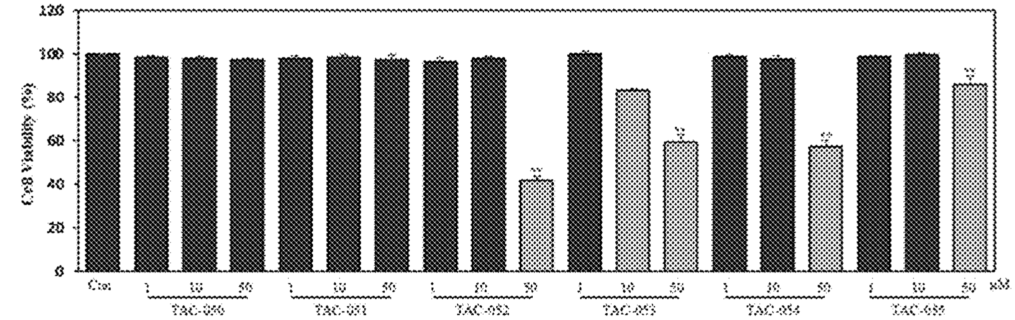
FIG. 7A-7C show the cytotoxicity and TNF-α secretion inhibitory effects of TAC5-050 to TAC5-055.

Unless defined otherwise, all technical and scientific terms used herein have the same meanings as appreciated by those skilled in the field to which the present invention pertains. In general, the nomenclature used herein is well-known in the art and is ordinarily used.

The present invention is based on the finding that novel compounds including compounds defined as TAC5 (TLR antagonistic compound 5)-050 to TAC5-055 inhibit the secretion of cytokines by inhibiting the TLR signaling pathway induced by TLR7 or TLR9 activation, which suggests that the compounds have therapeutic effects for autoimmune or inflammatory diseases such as systemic lupus erythematosus and psoriasis caused by TLR7 or TLR9 activation.

In one aspect, the present invention is directed to a compound represented by the following Formula 1 or a pharmaceutically acceptable salt thereof:

[Formula 1]

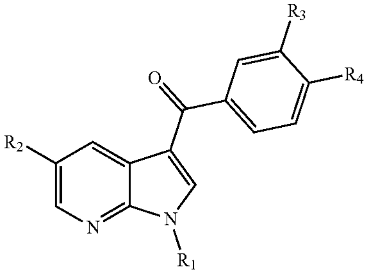

wherein $R_1$ to $R_4$ are the same as or different from each other, and are each independently a hydrogen atom, a halogen atom, straight- or branched-chain alkyl, amino, nitrile, nitro, nitroso, hydroxy, cycloalkyl, haloalkyl, allyl, alkoxy, alkylcarbonyl, cycloalkylcarbonyl, arylcarbonyl, alkylarylcarbonyl, alkoxycarbonyl, cycloalkoxy, aryl, heteroaryl, heterocycloalkyl, aryloxy, alkoxyheteroaryl, benzenesulfonyl, benzylsulfonyl, heteroaryloxyalkyl, alkylheteroaryl, alkylaryl, arylalkyl, alkylheteroaryl, alkylester, alkylamide or acryl, wherein the alkyl or the alkoxy is $C_{1-30}$ alkyl or alkoxy, the cycloalkyl is $C_{3-30}$ cycloalkyl, the allyl is $C_{2-30}$ allyl, the aryl is $C_{6-30}$ aryl, and the heteroaryl and the heterocycloalkyl contain a heteroatom selected from fluorine, oxygen, sulfur, and nitrogen.

As used herein, the term "$C_{1-30}$ alkyl" refers to a monovalent linear or branched saturated hydrocarbon moiety that has 1 to 30 carbon atoms and contains only carbon and hydrogen atoms. Examples of the alkyl group include, but are not limited to, methyl, ethyl, propyl, isopropyl, butyl, isobutyl, sec-butyl, tert-butyl, and the like. Examples of the "branched alkyl" include isopropyl, isobutyl, tert-butyl and the like.

As used herein, the term "$C_{1-30}$ alkoxy" refers to the formula —O—$_{1-30}$ alkyl and includes, but is not limited to, methoxy, ethoxy, isopropoxy, tert-butoxy and the like.

Specific examples of the term "halogen (or halo)" include fluorine (F), chlorine (Cl), bromine (Br) and iodine (I).

As used herein, the term "$C_{6-30}$ aryl" refers to a compound including at least one ring having a shared pi electron system, for example, a monocyclic or fused-ring polycyclic group (i.e., having rings sharing adjacent pairs of carbon atoms). That is, the aryl may include phenyl or biaryl such as naphthyl, unless otherwise defined herein. In one embodiment of the present invention, the aryl is an aromatic ring having 6 to 30 carbon atoms.

As used herein, the term "$C_{3-30}$ cyclic alkyl" refers to a cyclic saturated hydrocarbon moiety that has 5 to 6 carbon atoms and contains only carbon and hydrogen atoms. Examples of the cyclic alkyl group include, but are not limited to, cyclopentyl, cyclohexyl and the like.

As used herein, the term "heteroaryl" refers to an aromatic ring having 5 or 6 ring atoms containing 1 to 4 heteroatoms selected from the group consisting of N, O, and S, or a bicyclic ring having a heteroaryl ring fused to a benzene ring or another heteroaryl ring, unless otherwise defined. Examples of monocyclic heteroaryl include, but are not limited to, thiazolyl, oxazolyl, thiophenyl, furanyl, pyrrolyl, imidazolyl, isoxazolyl, isothiazolyl, pyrazolyl, triazolyl, triazinyl, thiadiazolyl, tetrazolyl, oxadiazolyl, pyridinyl, pyridazinyl, pyrimidinyl, pyrazinyl, and groups similar thereto. Examples of the bicyclic heteroaryl include, but are not limited thereto, indolyl, azaindolyl, indolinyl, benzothiophenyl, benzofuranyl, benzimidazolyl, benzooxazolyl, benzisoxazolyl, benzothiazolyl, benzothiadiazolyl, benzotriazolyl, quinolinyl, isoquinolinyl, purinyl, furopyridinyl, and groups similar thereto.

As used herein, the term "heterocycloalkyl" refers to a saturated or partially unsaturated carbocyclic ring having 5 to 9 ring atoms containing 1 to 3 heteroatoms selected from N, O, and S, in addition to carbon atoms. For example, the heterocycloalkyl may be azetidinyl, pyrrolidinyl, tetrahydrofuranyl, tetrahydrothienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, oxazepanyl, dihydroindolyl, dihydrofuryl, dihydroimidazolinyl, dihydrooxazolyl, tetrahydropyridinyl, dihydropyranyl, dihydrobenzofuranyl, benzodioxolyl, or benzodioxanyl.

As used herein, the alkyl, alkylamino or alkoxy is preferably $C_{1-20}$ alkyl, alkylamino or alkoxy, more preferably $C_{1-10}$ alkyl, alkylamino or alkoxy, most preferably $C_{1-3}$ alkyl, alkylamino or alkoxy.

As used herein, $R_1$ to $R_4$ may be substituents selected from the group consisting of the following substituents, but is not limited thereto.

$R_1$: hydrogen atom, $C_{1-3}$ alkyl, or benzenesulfonyl group; $R_2$: hydrogen atom or halogen atom; $R_3$: hydrogen atom, nitro group, or halogen atom; and $R_4$: hydrogen atom or halogen atom.

Preferably, the compound represented by Formula 1 may be selected from the group consisting of compounds represented by the following Formulas 1-1 to 1-6, but is not limited thereto.

[Formula 1-1]

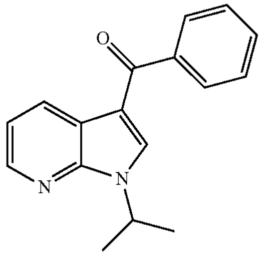

[Formula 1-2]

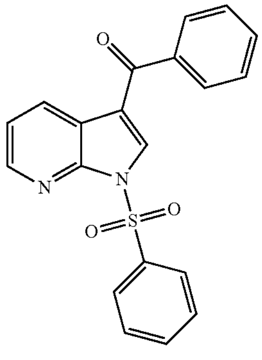

[Formula 1-3]

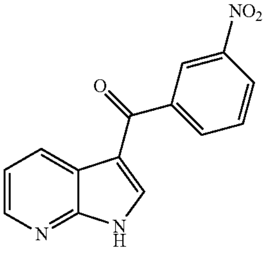

-continued

[Formula 1-4]

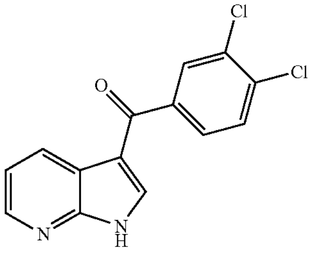

[Formula 1-5]

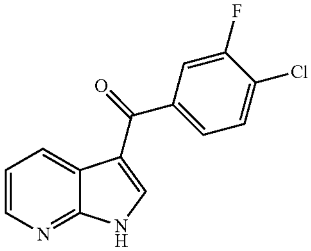

[Formula 1-6]

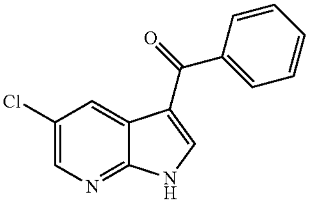

Here, the compound of Formula 1-1 is designated as "TAC5-050", the compound of Formula 1-2 is designated as "TAC5-051", the compound of Formula 1-3 is designated as "TAC5-052", the compound of Formula 1-4 is designated as "TAC5-053", the compound of Formula 1-5 is designated as "TAC5-054", and the compound of Formula 1-6 is designated as "TAC5-055" (Table 1).

TABLE 1

IUPAC name and molecular weight of compounds

| Name | IUPAC Name | MW(g/mol) |
|---|---|---|
| TAC5-050 | (1-Isopropyl-1H-pyrrolo[2,3-b]pyridin-3-yl)-phenyl-methanone | 264.33 |
| TAC5-051 | (1-Benzenesulfonyl-1H-pyrrolo[2,3-b]pyridin-3-yl)-phenyl-methanone | 362.40 |
| TAC5-052 | (3-Nitro-phenyl)-(1H-pyrrolo[2,3-b]pyridin-3-yl)-methanone | 267.24 |
| TAC5-053 | (3,4-Dichloro-phenyl)-(1H-pyrrolo[2,3-b]pyridin-3-yl)-methanone | 291.13 |
| TAC5-054 | (4-Chloro-3-fluoro-phenyl)-(1H-pyrrolo[2,3-b]pyridin-3-yl)-methanone | 274.68 |
| TAC5-055 | (5-Chloro-1H-pyrrolo[2,3-b]pyridin-3-yl)-phenyl-methanone | 256.69 |

The compound according to the present invention may be used in the form of a pharmaceutically acceptable salt, and an acid addition salt formed by pharmaceutically acceptable free acid is useful as the salt. The free acid may be an inorganic acid or organic acid. The inorganic acid includes hydrochloric acid, hydrobromic acid, sulfuric acid, phosphoric acid, and the like, and the organic acid includes citric acid, acetic acid, lactic acid, maleic acid, fumaric acid, gluconic acid, methanesulfonic acid, glycolic acid, succinic acid, tartaric acid, 4-toluenesulfonic acid, galacturonic acid, embonic acid, glutamic acid, aspartic acid, and the like.

The compound according to the present invention contains any salt, hydrate and solvate that can be prepared through conventional methods, along with the pharmaceutically acceptable salt.

In addition, the compound according to the present invention may be prepared in a crystalline or amorphous form. When the compound of Formula 1 is prepared in a crystalline form, it may optionally be hydrated or solvated.

In another aspect, the present invention is directed to a method of preparing a compound represented by the following Formula 1-1, the method including reacting a solution of phenyl(1H-pyrrolo[2,3-b]pyridin-3-yl)methanone in N,N-dimethylformamide (DMF) with sodium hydride and 2-iodopropane to synthesize (1-isopropyl-1H-pyrrolo[2,3-b]pyridin-3-yl)-phenyl-methanone.

[Formula 1-1]

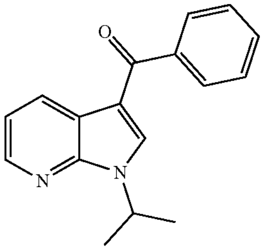

In another aspect, the present invention is directed to a method of preparing a compound represented by the following Formula 1-2, the method including reacting a solution of phenyl(1H-pyrrolo[2,3-b]pyridin-3-yl)methanone in N,N-dimethylformamide (DMF) with sodium hydride and benzenesulfonyl chloride to synthesize (1-benzylsulfonyl-1H-pyrrolo[2,3-b]pyridin-3-yl)-phenyl-methanone.

[Formula 1-2]

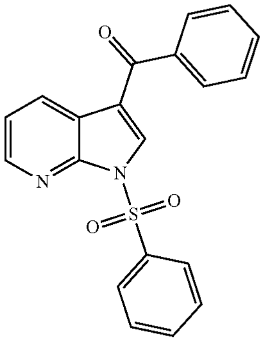

In the present invention, TAC5-050 to TAC5-055 of Table 1 may be prepared in accordance with a chemical synthesis method known in the art, and specifically, may be synthesized as follows.

According to an embodiment of the present invention, TAC5-050 may be prepared through a method including reacting a solution of phenyl(1H-pyrrolo[2,3-b]pyridin-3-yl)methanone in N,N-dimethylformamide (DMF) with sodium hydride and 2-iodopropane to synthesize (1-isopropyl-1H-pyrrolo[2,3-b]pyridin-3-yl)-phenyl-methanone.

According to an embodiment of the present invention, TAC5-051 may be prepared through a method including reacting a solution of phenyl(1H-pyrrolo[2,3-b]pyridin-3-yl)methanone in N,N-dimethylformamide (DMF) with sodium hydride and benzenesulfonyl chloride to synthesize (1-benzylsulfonyl-1H-pyrrolo[2,3-b]pyridin-3-yl)-phenyl-methanone.

According to an embodiment of the present invention, TAC5-052 may be prepared by dissolving 5-azaindole in methylene chloride (MC), adding $AlCl_3$ to the resulting solution, and then further adding p-nitrobenzoyl chloride thereto. In addition, TAC5-053 may be prepared by dissolving 5-azaindole in MC, adding $AlCl_3$ to the resulting solution, and then further adding 3,4-dichlorobenzoyl chloride thereto. TAC5-054 may be prepared by reacting 4-chloro-3-fluorobenzoic acid with $SOCl_2$ to synthesize 4-chloro-3-fluorobenzoyl chloride and then adding a solution of 5-azaindole in MC and $AlCl_3$ thereto. In addition, TAC5-055 may be prepared by dissolving 5-chloro-azaindole in MC, adding $AlCl_3$ to the resulting solution, and then further adding benzoylchloride thereto.

In the present invention, the compound represented by Formula 1 exhibits an effect of inhibiting the secretion of inflammatory cytokines such as TNF-α by inhibiting the TLR7 or TLR9 signaling pathway.

Accordingly, in another aspect, the present invention is directed to a TLR7 or TLR9 inhibitor containing the compound represented by Formula 1 or a pharmaceutically acceptable salt thereof.

The compound inhibiting TLR7 or TLR9 signaling pathway may preferably have a structure represented by Formula 1-1 or Formula 1-2, but is not limited thereto.

According to an embodiment of the present invention, it was found that TAC5-050 or TAC5-051 inhibits overactivation of cytokines such as TNF-α by inhibiting the TLR signaling pathway induced by TLR7 or TLR9 activation. Therefore, TAC5-050 or TAC5-051 has excellent effects of reducing inflammatory cytokines (ameliorating inflammatory response) and thus can be useful as a composition for preventing or treating autoimmune diseases and inflammatory diseases caused by TLR7 or TLR9 activation.

As used herein, the term "TLR7" refers to a protein that is categorized as a toll-like receptor (TLRs) which is a family of transmembrane proteins that function as monitors for pathogen infection, is a protein encoded by a TLR7 gene, and is also called UNQ248/PRO285. The TLR7 recognizes ssRNA (single-stranded RNA) of an RNA virus or synthetic small molecules, imidazoquinoline, loxoribine and bropirimine to activate the innate immune system.

As used herein, the term "TLR9" refers to a protein that is categorized as a toll-like receptor (TLR) which is a family of transmembrane proteins that function as monitors for pathogen infection, is a protein encoded by a TLR9 gene, and is also called CD289 or UNQ5798/PRO19605. The TLR9 recognizes unmethylated CpG oligodeoxynucleotide DNA fragments from bacteria or DNA viruses to activate the innate immune system.

As used herein, the term "TLR-signaling pathway" refers to a signaling pathway through TLR, which may be a reaction that depends on a complex formed by TLR and the adapter protein MyD88 (for TLR7/8/9) or a complex formed by TLR and the adapter protein TRIF (for TLR3) and functions to transmit a signal. Activated TLR7/8/9 activates NF-κB through a Myd88-dependent signaling process, moves to the nucleus, and induces activation of MAPK. The activation of NF-κK and MAPK causes inflammatory cytokines such as TNF-α, IL-1β and IL-6 to be secreted and oxidative stressors such as nitrogen monoxide (hereinafter referred to as NO) and reactive oxygen species (hereinafter referred to as ROS) to be produced in macrophages. In addition, TLR3 activates TRIF, interferon-regulator (IRF), and NF-κB, thus inducing MyD88-independent signaling process and secretion of type 1 interferon.

As used herein, the term "TIR domain" refers to a domain that is used for intracellular signaling, has three highly conserved regions, and mediates the interaction between TLR and other signaling molecules. In an activated reaction, the TIR domain induces binding with MyD88 or TRIF and activates the TLR-signaling pathway.

As used herein, the term "inhibition" refers to a phenomenon in which biological activity or signaling activity is deteriorated due to some deficiency, imbalance or other causes, and may include partial or complete blocking, reduction or prevention of activity of TLR, delaying of activation, inactivation, or down-regulation.

As used herein, the term "inhibitor" refers to a molecule that partially or completely inhibits influences on other molecules such as receptors or intracellular mediators by any mechanism.

As used herein, the term "TLR7 or TLR9 inhibitor" refers to a substance that is capable of directly, indirectly, or substantially interfering with, reducing or inhibiting the biological activity of TLR7 or TLR9, preferably a substance that is capable of reducing the secretion of NF-KB, MAPK, inflammatory cytokines, NO, and ROS by binding to TLR7 or TLR9 receptors, neutralizing the activity thereof, and thereby blocking TLR7- or TLR9-signaling pathways.

In another aspect, the present invention is directed to a pharmaceutical composition for preventing or treating an autoimmune disease or an inflammatory disease containing the compound represented by Formula 1 or a pharmaceutically acceptable salt thereof.

In another aspect, the present invention is directed to a method for preventing or treating an autoimmune disease or an inflammatory disease including administering the compound represented by Formula 1 to a subject.

In another aspect, the present invention is directed to the use of the compound for the prevention or treatment of an autoimmune disease or inflammatory disease.

In another aspect, the present invention is directed to the use of the compound for the preparation of a drug for preventing or treating an autoimmune disease or inflammatory disease.

In the present invention, the compound represented by Formula 1 may be selected from the group consisting of the compounds of Formulas 1-1 to 1-6, but is not limited thereto.

In the present invention, the autoimmune disease or inflammatory disease is selected from the group consisting of psoriasis, systemic lupus erythematosus (SLE), skin rash, photosensitivity, arthritis, oral ulcer, nephritis, hemocytopenia, vasculitis, serositis, inflammatory bowel disease (IBD), diabetes, multiple sclerosis, skin sclerosis, pemphigus, atopic dermatitis, urethritis, cystitis, arteriosclerosis, allergic diseases, rhinitis, asthma, acute pain, chronic pain, periodontitis, gingivitis, gout, myocardial infarction, congestive heart failure, high blood pressure, angina pectoris, gastric ulcer, cerebral infarction, Down's syndrome, obesity, dementia, depression, schizophrenia, tuberculosis, sleep disorders, sepsis, burns, pancreatitis, Parkinson's disease, and stroke, but is not limited thereto.

As used herein, the term "autoimmune disease" refers to a disease caused by a process in which a problem occurs in inducing or maintaining self-tolerance, leading to an immune response to a self-antigen and thus an attack on the organism's own tissue. The term "self-tolerance" refers to immunologic unresponsiveness, meaning the lack of harmful response to a potentially antigenic substance constituting the self An autoimmune disease includes a disease resulting from the breakdown of self-resistance in which an adaptive immune system responds to a self-antigen and mediates cellular and tissue damage. In certain embodiments, the autoimmune disease results at least partially from a humoral immune response.

Autoimmune diseases pertinent to the present invention include systemic lupus erythematosus, insulin-dependent diabetes mellitus, multiple sclerosis, autoimmune encephalomyelitis, rheumatoid arthritis, autoimmune arthritis, myasthenia gravis, thyroiditis, experimental uveitis, Hashimoto's thyroiditis, primary myxedema, thyroid toxicosis, pernicious anemia, autoimmune atrophic gastritis, Addison's disease, early menopause, male infertility, childhood diabetes, Goodpasture syndrome, pemphigus vulgaris, bullous pemphigoid, sympathetic ophthalmitis, lens uveitis, autoimmune hemolytic anemia, idiopathic leukocytosis, primary biliary cirrhosis, chronic active hepatitis Hbs-ve, latent cirrhosis, ulcerative colitis, Sjogren's syndrome, scleroderma, Wegener's granulomatosis, polymyositis/dermatomyositis, and discoid LE, but are not limited thereto.

In addition, non-limiting examples of the autoimmune disease include acute disseminated encephalomyelitis (ADEM), acute necrotizing hemorrhagic leukoencephalitis, Addison's disease, agammaglobulinemia, allergic asthma, allergic rhinitis, alopecia areata, amyloidosis, ankylosing spondylitis, antibody-mediated transplant rejection, anti-GBM/anti-TBM nephritis, antiphospholipid antibody syndrome (APS), autoimmune angioedema, autoimmune aplastic anemia, autoimmune autonomic dystrophy, autoimmune hepatitis, autoimmune hyperlipidemia, autoimmune immunodeficiency syndrome, autoimmune inner-ear disease (AIED), autoimmune myocarditis, autoimmune pancreatitis, autoimmune diabetic retinopathy, autoimmune thrombocytopenia purpura (ATP), autoimmune thyroid disease, autoimmune urticaria, axon and neuronal neuropathy, Balo disease, Bechet's disease, pemphigus, cardiomyopathy, Castleman's disease, celiac disease, Chagas disease, chronic fatigue syndrome, chronic inflammatory demyelinating polyneuropathy (CIDP), chronic recurrent multifocal osteomyelitis (CRMO), Churg-Strauss syndrome, scarring pemphigus/benign mucosal pemphigus, Crohn's disease, Cogan syndrome, cold agglutinin disease, congenital heart blockage, coxsackie myocarditis, CREST disease, essential mixed cryoglobulinemia, demyelinating neuropathies, herpetic dermatitis, dermatitis, Devic's disease (optic neuromyelitis), discoid lupus, Dressler's syndrome, endometriosis, eosinophilic fasciitis, nodular erythema, experimental allergic encephalomyelitis, Evans syndrome, fibromyalgia, fibrous alveolitis, giant-cell arteritis (temporal arteritis), glomerulonephritis, Goodpasture syndrome, granulomatosis with polyangiitis (GPA), Graves' disease, Guillain-Barre syndrome, Hashimoto's encephalitis, Hashimoto thyroiditis, hemolytic anemia, Henoch-Schoenlein purpura, gestational herpes, hypogammaglobulinemia, hypergammaglobulinemia, idiopathic thrombocytopenia purpura (ITP), IgA kidney disease, IgG4-related sclerotic disease, immunomodulatory lipoprotein, inclusion body myositis, inflammatory bowel disease, insulin-dependent diabetes (type 1), interstitial cystitis, juvenile arthritis, juvenile diabetes, Kawasaki syndrome, Eaton-Lambert syndrome, leukopenia vasculitis, lichen planus, lichen sclerosis, ligneous conjunctivitis, linear IgA disease (LAD), lupus (SLE), Lyme disease, Meniere's disease, microscopic polyangiitis, mixed connective tissue disease (MCTD), monoclonal gammopathy of undetermined significance (MGUS), encroaching corneal ulcer, Mucha-Habermann disease, multiple sclerosis, myasthenia gravis, myositis, narcolepsy, neuromyelitis (Devic's disease), neutropenia, ocular cicatricial pemphigoid, optic neuritis, recurrent rheumatism, PANDAS (pediatric autoimmune neuropsychiatric disorders associated with streptococcal infections), antitumor cerebellar degeneration, paroxysmal nocturnal hemoglobinuria (PNH), facial unilateral atrophy, Parsonage-Turner syndrome, pars planitis (peripheral uveitis), pemphigus, peripheral neuropathy, perivenous encephalomyelitis, pernicious anemia, POEMS syndrome, polyarteritis nodosa, type I, type II, and type III autoimmune polyglandular syndrome, multiple muscle pain rheumatism, polymyositis, post-myocardial-infarction syndrome, post-pericardiectomy syndrome, progesterone dermatitis, primary biliary cirrhosis, primary sclerosing cholangitis, psoriasis, psoriatic arthritis, idiopathic pulmonary fibrosis, gangrene pyoderma, pure red blood cell aplasia, Raynaud's phenomenon, reflex sympathetic dystrophy, Reiter's syndrome, recurrent polychondritis, restless legs syndrome, retroperitoneal fibrosis, rheumatoid fever, rheumatoid arthritis, sarcoidosis, scimitar syndrome, scleritis, scleroderma, Sjogren's syndrome, sperm and testicular autoimmunity, stiff person syndrome, subacute bacterial endocarditis (SBE), Susac's syndrome, sympathetic ophthalmitis, Takayasu's arteritis, temporal arteritis/giant-cell arteritis, thrombocytopenic purpura (TTP), Tolosa-Hunt syndrome, transverse myelitis, ulcerative colitis, undifferentiated connective tissue disease (UCTD), uveitis, vasculitis, vesiculobullous dermatosis, vitiligo, Waldenstrom macroglobulinemia (WM), and Wegener's granulomatosis (granulomatosis with polyangiitis; GPA).

As used herein, the term "inflammatory disease" refers to a disease caused by an inflammatory substance (inflammatory cytokine) such as TNFα, IL-1, IL-6, prostaglandin, leukotriene or NO secreted by immune cells such as macrophages due to excessive excitation of the immune system by harmful stimulation such as inflammation-inducing factors or irradiation. The "inflammatory disease" may be an acute or chronic inflammatory condition, and may be caused by an infectious or non-infectious factor.

The inflammatory disease of the present invention includes psoriasis, asthma, eczema, allergies, rheumatoid arthritis, psoriatic arthritis, contact dermatitis, atopic dermatitis, acne, atopic rhinitis, allergic dermatitis, chronic sinusitis, seborrheic dermatitis, gastritis, gout, gouty arthritis, ulcers, chronic bronchitis, pulmonary inflammation, Crohn's disease, ulcerative colitis, ankylosing spondylitis, sepsis, vasculitis, bursitis, lupus, rheumatoid polymyalgia, temporal arteritis, multiple sclerosis, solid cancer, Alzheimer's disease, arteriosclerosis, obesity and viral infections, but is not limited thereto.

In addition, non-limiting examples of the inflammatory disease include atherosclerosis, arteriosclerosis, autoimmune disorders, multiple sclerosis, systemic lupus erythematosus, multiple muscle pain rheumatism (PMR), gouty arthritis, degenerative arthritis, tendinitis, bursitis, psoriasis, cystic fibrosis, osteoarthritis, rheumatoid arthritis, inflammatory arthritis, Sjogren's syndrome, giant-cell arteritis, progressive systemic sclerosis (scleroderma), ankylosing spondylitis, polymyositis, dermatitis, pemphigus, pemphigoid, diabetes (e.g., type I diabetes), myasthenia gravis, Hashimoto's thyroiditis, Graves' disease, Goodpasture disease, mixed connective tissue disease, sclerosing cholangitis, inflammatory bowel disease, Crohn's disease, ulcerative colitis, pernicious anemia, inflammatory skin disease, usual interstitial pneumonia (UIP), asbestos diseases, silicosis, bronchiectasis, beryllium poisoning, talcosis, pneumoconiosis, sarcoidosis, detachable interstitial pneumonia, lymphocytic interstitial pneumonia, giant-cell interstitial pneumonia, cellular interstitial pneumonia, exogenous allergic alveolitis, Wegener's granulomatosis and vasculitis-associated forms (temporal arteritis and polyarteritis nodosa), inflammatory skin disease, hepatitis, delayed-type hypersensitivity (e.g. poison ivy dermatitis), pneumonia, airway inflammation, adult respiratory disorder syndrome (ARDS), encephalitis, immediate hypersensitivity, asthma, hay fever, allergies, acute anaphylaxis, rheumatic fever, glomerulonephritis, pyelonephritis, cellulitis, cystitis, chronic cholecystitis, ischemia (ischemic injury), allograft rejection, host-to-transplant rejection, appendicitis, arteritis, blepharitis, bronchiolitis, bronchitis, cervicitis, cholangitis, chorionic amnionitis, conjunctivitis, psoriasis, dermatitis, endocarditis, endometritis, enteritis, intestinal inflammation, epididymitis, fasciitis, connective tissue infection, gastritis, gastroenteritis, gingivitis, ileitis, iritis, laryngitis, myocarditis, nephritis, omphalitis, ovaritis, orchitis, osteitis, otitis, pancreatitis, mumps, pericarditis, pharyngitis, nephritis, phlebitis, interstitial pneumonia, rectal analitis, prostatitis, rhinitis, salpingitis, sinusitis, stomatitis, synovitis, orchitis, tonsillitis, urethritis, urocystitis, uveitis, vaginitis, vasculitis, vulvitis, vulvovaginitis, vasculitis, chronic bronchiolitis, osteomyelitis, optic neuritis, temporal arteritis, transverse myelitis, cerebral fasciitis, and cerebral encephalopathy. In certain embodiments, the inflammatory disease is selected from the group consisting of atherosclerosis, arteriosclerosis, autoimmune disorders, multiple sclerosis, systemic lupus erythematosus, rheumatoid arthritis, inflammatory arthritis, and myocarditis.

As herein used, the term "prevention" means any action that inhibits or delays an autoimmune disease and/or an inflammatory disease by administration of the pharmaceutical composition containing the compound or a pharmaceutically acceptable salt thereof. As used herein, the term "treatment" means any action that ameliorates or completely cures the symptoms of an autoimmune disease and/or an inflammatory disease by administration of the pharmaceutical composition containing the compound of Formula 1 or a pharmaceutically acceptable salt thereof.

The composition for preventing or treating an autoimmune disease and/or inflammatory disease according to the present invention may contain a pharmaceutically effective amount of the compound represented by Formula 1 alone, or may further contain at least one pharmaceutically acceptable carrier, excipient or diluent, in addition to the compound. The term "pharmaceutically effective amount" refers to an amount sufficient to prevent, ameliorate, and treat symptoms of an autoimmune disease and/or an inflammatory disease.

The term "pharmaceutically acceptable" used herein means being physiologically acceptable without causing ordinary allergic reactions such as gastrointestinal disorders or dizziness or similar reactions thereto when administration to humans. Examples of the carrier, excipient and diluent include lactose, dextrose, sucrose, sorbitol, mannitol, xylitol, erythritol, maltitol, starch, gum acacia, alginate, gelatin, calcium phosphate, calcium silicate, cellulose, methyl cellulose, polyvinylpyrrolidone, water, methylhydroxybenzoate, propylhydroxybenzoate, talc, magnesium stearate, and mineral oils. In addition, the composition may further contain fillers, anti-aggregating agents, lubricants, wetting agents, flavoring agents, emulsifying agents, and preservatives.

As used herein, the term "carrier" refers to a substance that facilitates the addition of a compound to a cell or tissue.

As used herein, the term "diluent" is defined as a substance that stabilizes the biological activity of a subject compound and is diluted in water to dissolve the compound.

In addition, the composition of the present invention may contain one or more known active ingredients having a therapeutic effect on autoimmune diseases and/or inflammatory diseases along with the compound represented by Formula 1.

The composition of the present invention may be formulated using a method known in the art to provide rapid, sustained, or delayed release of the active ingredient after administration to a non-human mammal. The formulation may be in the form of a powder, granule, tablet, emulsion, syrup, aerosol, soft or hard gelatin capsule, a sterile injectable solution, or sterile powder.

The composition of the present invention may be administered through various routes, including oral, transdermal, subcutaneous, intravenous or intramuscular administration, and the dosage of the active ingredient depends on various factors such as the route of administration, the patient's age, gender and weight, and the severity of disease of the patient. The composition according to the present invention may be administered in combination with a known compound having an effect of preventing, ameliorating or treating symptoms of autoimmune diseases and/or inflammatory diseases.

Other terms and abbreviations used in the present specification may be interpreted as having meanings commonly understood by those skilled in the art to which the present invention pertains, unless otherwise defined.

Hereinafter, the present invention will be described in more detail with reference to the following examples. However, it will be obvious to those skilled in the art that the following examples are merely provided for illustration of the present invention, and should not be construed as limiting the scope of the present invention.

PREPARATION EXAMPLE $^1H$ and $^{13}C$ NMR spectra were recorded using JNM-ECZ400S (JEOL, Japan), and the chemical shift was measured within the downfield range of ppm of the internal tetramethylsilane standard.

Multiplicity is expressed as follows: s (singlet); d (doublet); t (triplet); q (quartet); m (multiplet); dd (doublet of doublet); ddd (doublet of doublet of doublet); dt (doublet of triplet); td (triplet of doublet); brs (broad singlet).

The coupling constant was recorded as H. Routine mass analyses were performed using an LC/MS system equipped with a reverse-phase column (C-18, 50×2.1 mm, 5 μm) and electron spray ionization (ESI).

The progress of the reaction was monitored using TLC (silica gel 60 F254 0.25 mm), and the components were visualized by observation under UV light (254 nm, 365 nm) or by heating after treating the TLC plate with anisaldehyde, $KMNO_4$, and phosphomolybdic acid. Unless otherwise specified, all reactions were carried out in oven-dried glassware under a dry argon atmosphere.

Methylene chloride (MC), 5-azaindole, benzoyl chloride, N,N-dimethylformamide (DMF), 2-iodopropane, benzenesulfonyl chloride, p-nitrobenzoyl chloride, 3,4-dichlorobenzoyl chloride, 4-chloro-3-fluorobenzoic acid and 5-chloroazaindole were obtained from Sigma-Aldrich Co. (St. Louis, MO, USA).

Preparation Example 1

Preparation of phenyl(1H-pyrrolo[2,3-b]pyridin-3-yl)methanone

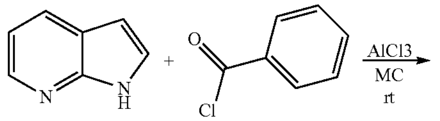

$C_7H_6N_2$
Mol. Wt.: 118.14
1

$C_7H_5ClO$
Mol. Wt.: 140.57
2

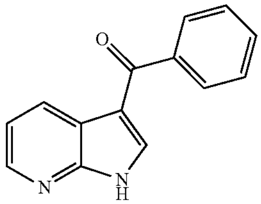

$C_{14}H_{10}N_2O$
Mol. Wt.: 222.24
3

1.49 g (12.6 mmol) of 5-azaindole was dissolved in 150 ml of MC, and 8.4 g (105 mmol, 5 eq) of $AlCl_3$ was added to the resulting solution, followed by stirring at room temperature for 1 hour. A solution of 3.45 g (24.6 mmol) of benzoyl chloride in 10 ml of MC was added dropwise to the reaction solution at room temperature. After 1 hour, TLC was performed. When the reaction was completed, the solvent was removed by concentration under reduced pressure. The reactor containing the concentrated residue was placed in an ice bath, 30 g of ice water was added thereto, and then stirred for 1 hour. Then, the result was filtered and washed with water. The solid was dissolved in 30 mL of MC and 10 mL of MeOH, and washed with 30 mL of Sat'd $NaHCO_3$, and the layers were separated. The MC layer was washed with water, and the organic layer was dried over $MgSO_4$, filtered, and concentrated under reduced pressure. After refluxing in 20 ml of IPA, the result was stirred at room temperature for 1 hour and then filtered. The solid was refluxed in 20 ml of MC, stirred at room temperature for 1 hour, and filtered to prepare phenyl(1H-pyrrolo[2,3-b]pyridin-3-yl)methanone. The yield was 1.17 g/2.8=41.8%, and EA/Hex=1/2.

Preparation Example 2

Preparation of (1-isopropyl-1H-pyrrolo[2,3-b]pyridin-3-yl)-phenyl-methanone (TAC5-050)

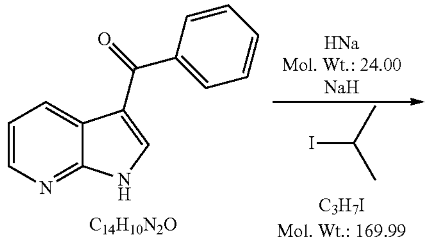

$C_{14}H_{10}N_2O$
Mol. Wt.: 222.24
1

$C_3H_7I$
Mol. Wt.: 169.99
2

-continued

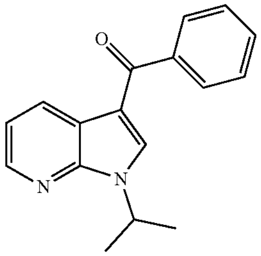

$C_{17}H_{16}N_2O$
Mol. Wt.: 264.32
3

0.33 g (1.48 mmol) of phenyl(1H-pyrrolo[2,3-b]pyridin-3-yl)methanone was dissolved in 20 ml of DMF and the resulting solution was then cooled to −20° C. 89 mg (1.5 eq) of 60% NaH was added to the reactor and the temperature change was observed. After stirring for 1 hour at the same temperature, 0.3 g of 2-iodopropane and 5 ml of DMF were slowly added to the reaction solution. After stirring at the same temperature for 3 hours, TLC was performed (EA:Hex=1:3) and then stirred overnight at room temperature. After completion of the reaction, 30 ml of EA and 20 ml of Sat'd $NH_4Cl$ were added to the reaction solution, followed by stirring for 30 minutes and layer separation. The organic layer was washed with 30 mL of water, treated with $MgSO_4$, filtered, and concentrated under reduced pressure. The concentrated residue was subjected to column separation in the presence of EA:Hex=1:10 to obtain 0.18 g of (1-isopropyl-1H-pyrrolo[2,3-b]pyridin-3-yl)-phenyl-methanone. The yield was 0.18/0.39=46.15%.

NMR data is shown in FIG. 1A. $^1H$ NMR (300 MHz, DMSO-d6) δ 1.59 (d, 6H), 5.29 (m, 1H), 7.24 (dd, 1H), 7.53 (dd, 1H), 7.58 (dd, 1H), 7.80 (s, 1H), 7.82 (d, 1H), 8.43 (d, 1H), 8.65 (d, 1H). HPLC data are shown in FIG. 1B. Mobile Conditions: MeOH/$H_2O$=7/3, λmax=250 nm. TLC data are shown in FIG. 1C. EA/Hex=1/2.

Preparation Example 3

Preparation of (1-benzenesulfonyl-1H-pyrrolo[2,3-b]pyridin-3-yl)-phenyl-methanone (TAC5-051)

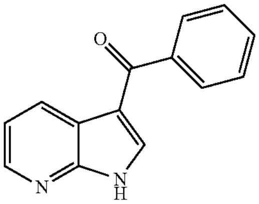

+

$C_{14}H_{10}N_2O$
Mol. Wt.: 222.24
1

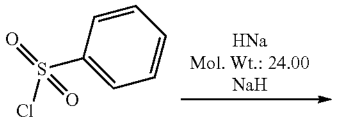

$C_6H_5ClO_2S$
Mol. Wt.: 176.62
2

-continued

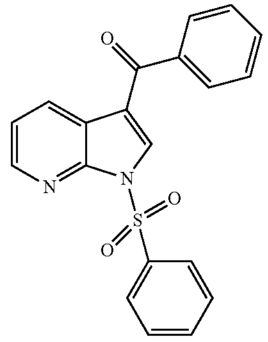

$C_{20}H_{14}N_2O_3S$
Mol. Wt.: 362.40
3

0.33 g (1.48 mmol) of phenyl(1H-pyrrolo[2,3-b]pyridin-3-yl)methanone was dissolved in 5 ml of DMF, the resulting solution was cooled to −10° C., and 77 mg (1.3 eq) of 60% NaH was added to the reactor and the reactor was allowed to warm to room temperature. The mixture was stirred at room temperature for 1 hour. 0.31 g (1.2 eq.) of benzene-sulfonyl chloride and 5 ml of DMF were slowly added to the reaction solution at 0° C. After stirring at 0° C. for 2 hours, TLC (EA:Hex=1:1) was performed. 70 ml of EA and 70 ml of water were sequentially added, followed by stirring for 20 minutes and layer separation. The aqueous layer was identified by TLC. If there was a product, extraction was performed one more time. The EA layer was concentrated under reduced pressure. The concentrated residue was subjected to column separation in the presence of EA:Hex=1:4, but was not purified. The residue was concentrated and then recrystallized in 20 ml MeOH to obtain 0.21 g of (1-benzenesulfonyl-1H-pyrrolo[2,3-b]pyridin-3-yl)-phenyl-methanone. The yield was 39%.

NMR data are shown in FIG. 2A. $^1$H NMR (300 MHz, DMSO-d6) δ 7.42 (dd, 1H), 7.59~7.63 (m, 4H), 7.68 (dd, 2H), 7.91 (d, 2H), 8.21 (d, 2H), 8.28 (s, 1H), 8.44 (d, 1H), and 8.49 (d, 1H). HPLC data is shown in FIG. 2B. Mobile Conditions: MeOH/$H_2O$=7/3, λmax=250 nm. TLC data is shown in FIG. 2C. EA/Hex=1/2.

Preparation Example 4

Preparation of (3-nitro-phenyl)-(1H-pyrrolo[2,3-b]pyridin-3-yl)-methanone (TAC5-052)

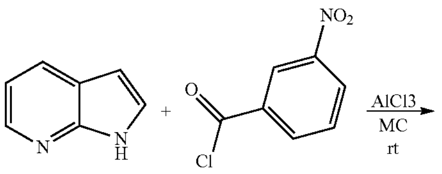

$C_7H_6N_2$
Mol. Wt.: 118.14
1

$C_7H_4ClNO_3$
Mol. Wt.: 185.56
2

-continued

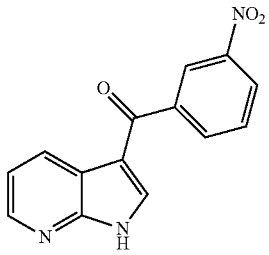

$C_{14}H_9N_3O_3$
Mol. Wt.: 267.24
3

0.5 g (4.2 mmol) of 5-azaindole was dissolved in 50 ml of MC, and 2.8 g (21 mmol, 5 eq) of $AlCl_3$ was added thereto, followed by stirring at room temperature for 1 hour. A solution of 2.28 g (12.3 mmol) of p-nitrobenzoyl chloride in 10 ml of MC was added dropwise to the reaction solution at room temperature. The mixture was stirred overnight. When the reaction was completed, the reactor containing the concentrated residue was placed in an ice bath, 30 g of ice water was added thereto, and then stirred for 1 hour. Then, the result was filtered and washed with water. The solid was dissolved in 30 mL of MC and 10 mL of MeOH, and washed with 30 mL of Sat'd $NaHCO_3$, and the layers were separated. The MC layer was washed with water, and the organic layer was dried over $MgSO_4$, filtered, and concentrated under reduced pressure. After refluxing in 20 ml of IPA, the result was stirred at room temperature for 1 hour and then filtered. The solid was refluxed in 20 ml of MC, stirred at room temperature for 1 hour, and filtered to prepare 85 mg of (3-nitro-phenyl)-(1H-pyrrolo[2,3-b]pyridin-3-yl)-methanone (yield: 7.5%). However, it was not easy to remove impurities, so the yield was low and solubility was also low.

NMR data are shown in FIG. 3A. $^1$H NMR (300 MHz, DMSO-d6) δ 7.30 (dd, 1H), 7.80 (t, 1H), 8.21 (d, 1H), 8.23 (s, 1H), 8.36 (d, 1H), 8.42 (d, 1H), 8.46(d, 1H), 8.52 (d, 1H). HPLC data are shown in FIG. 3B. Mobile Conditions: MeOH/$H_2O$=6/4, λmax=250 nm. TLC data are shown in FIG. 3C. EA/Hex=1/2.

Preparation Example 5

Preparation of (3,4-dichloro-phenyl)-(1H-pyrrolo[2,3-b]pyridin-3-yl)-methanone (TAC5-053)

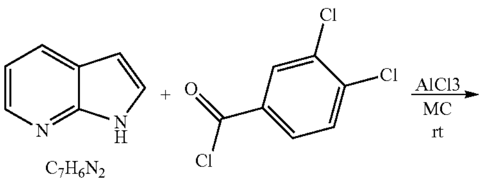

$C_7H_6N_2$
Mol. Wt.: 118.14
1

$C_7H_3Cl_3O$
Mol. Wt.: 209.46
2

-continued

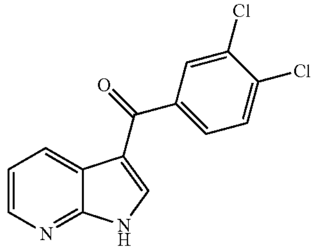

$C_{14}H_8Cl_2N_2O$
Mol. Wt.: 291.13
3

0.5 g (4.2 mmol) of 5-azaindole was dissolved in 50 ml of MC, and 2.8 g (21 mmol, 5 eq) of $AlCl_3$ was added to the resulting solution, followed by stirring at room temperature for 1 hour. A solution of 2.58 g (12.3 mmol) of 3,4-dichlorobenzoyl chloride in 10 ml of MC was added dropwise to the reaction solution at room temperature. The mixture was stirred overnight. When the reaction was completed, the reaction solution was concentrated under reduced pressure to remove the solvent. The reactor containing the concentrated residue was added to an ice bath, and 30 g of ice water was added thereto, followed by stirring for 1 hour to obtain 0.52 g of (3,4-dichloro-phenyl)-(1H-pyrrolo[2,3-b]pyridin-3-yl)-methanone (yield: 42.6%).

NMR data are shown in FIG. 4A. $^1$H NMR (300 MHz, DMSO-d6) δ 7.28 (dd, 1H), 7.75 (d, 1H), 7.78 (d, 1H), 7.95 (d, 1H), 8.19 (s, 1H), 8.34 (d, 1H), and 8.48 (d, 1H). HPLC data are shown in FIG. 4B. Mobile Conditions: MeOH/$H_2O$=7/3, λmax=250 nm. TLC data are shown in FIG. 4C. EA/Hex=1/2.

Preparation Example 6

Preparation of (4-chloro-3-fluoro-phenyl)-(1H-pyrrolo[2,3-b]pyridin-3-yl)-methanone (TAC5-054)

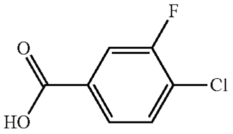

$C_7H_4ClFO_2$
Mol. Wt.: 174.56
A

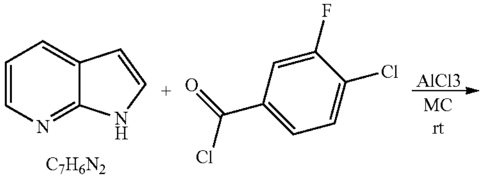

$C_7H_6N_2$
Mol. Wt.: 118.14
1

$C_7H_3Cl_2FO$
Mol. Wt.: 193.00
2

-continued

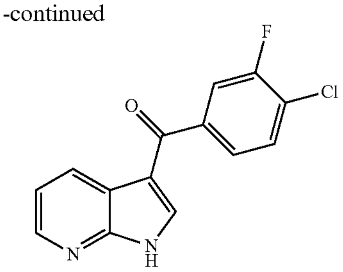

$C_{14}H_8ClFN_2O$
Mol. Wt.: 274.68
3

2.38 g (13.6 mmol) of 4-chloro-3-fluorobenzoic acid, 3.12 g (26.2 mmol) of $SOCl_2$ and 20 ml of toluene were refluxed overnight and concentrated under reduced pressure three times to remove the toluene and $SOCl_2$, thereby synthesize 4-chloro-3-fluorobenzoyl chloride.

0.5 g (4.2 mmol) of 5-azaindole was dissolved in 50 ml of MC, 2.8 g (21 mmol, 5 eq) of $AlCl_3$ was added to the resulting solution, followed by stirring at room temperature for 1 hour. A solution of 2.38 g (12.3 mmol) of the concentrated residue of 4-chloro-3-fluorobenzoyl chloride in 10 ml of MC was added dropwise to the reaction solution at room temperature and the mixture was stirred overnight. When the reaction was completed, the reaction solution was concentrated under reduced pressure to remove the solvent. The reactor containing the concentrated residue was added to an ice bath, and 30 g of ice water was added thereto, followed by stirring for 1 hour. Then, the result was filtered and washed with water. The solid was dissolved in 30 mL of MC and 10 mL of MeOH, and washed with 30 mL of Sat'd $NaHCO_3$, and the layers were separated. The MC layer was washed with water, and the organic layer was dried over $MgSO_4$, filtered, and concentrated under reduced pressure. After refluxing in 20 ml of IPA, the result was stirred at room temperature for 1 hour and then filtered. The solid was refluxed in 20 ml of MC, stirred at room temperature for 1 hour, and filtered to obtain 0.31 g of (4-chloro-3-fluoro-phenyl)-(1H-pyrrolo[2,3-b]pyridin-3-yl)-methanone (yield: 30%).

NMR data are shown in FIG. 5A. $^1$H NMR (300 MHz, DMSO-d6) δ 7.28 (dd, 1H), 7.64 (d, 1H), 7.73 (d, 1H), 7.76 (d, 1H), 8.19 (s), 1H), 8.34 (d, 1H), and 8.48 (d, 1H). HPLC data are shown in FIG. 5B. Mobile Conditions: MeOH/$H_2O$=7/3, λmax=250 nm. TLC data is shown in FIG. 5C. EA/Hex=1/2.

Preparation Example 7

Preparation of (5-chloro-1H-pyrrolo[2,3-b]pyridin-3-yl)-phenyl-methanone (TAC5-055)

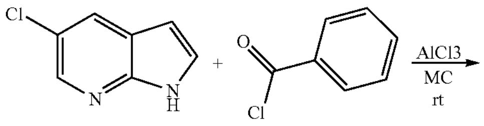

$C_7H_5ClN_2$
Mol. Wt.: 152.58
1

$C_7H_5ClO$
Mol. Wt.: 140.57
2

-continued

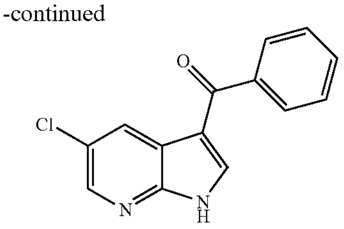

$C_{14}H_9ClN_2O$
Mol. Wt.: 256.69

3

0.64 g (4.2 mmol) of 5-chloro-azaindole was dissolved in 50 ml of MC, and 2.8 g (21 mmol, 5 eq) of $AlCl_3$ was added to the resulting solution, followed by stirring at room temperature for 1 hour. A solution of 1.73 g (12.3 mmol) of benzoylchloride in 10 ml of MC was added dropwise to the reaction solution at room temperature. The mixture was stirred overnight. When the reaction was completed, the reaction solution was concentrated under reduced pressure to remove the solvent. The reactor containing the concentrated residue was added to an ice bath, and 30 g of ice water was added thereto, followed by stirring for 1 hour to obtain 0.37 g of (5-chloro-1H-pyrrolo[2,3-b]pyridin-3-yl)-phenyl-methanone (yield: 34.3%).

NMR data are shown in FIG. 6A. $^1H$ NMR (300 MHz, DMSO-d6) δ 7.53 (dd, 2H), 7.59 (m, 1H), 7.78 (d, 2H), 8.18 (s, 1H), 8.36(d, 1H), and 8.48 (d, 1H). HPLC data are shown in FIG. 6B. Mobile Conditions: $MeOH/H_2O=7/3$, λmax=250 nm. The TLC data are shown in FIG. 6C. EA/Hex=1/1 and EA/Hex=1/3.

EXAMPLE

RAW264.7 cells, which are murine macrophages (ATCC, Manassas, VA, USA), were incubated in low-glucose DMEM (Thermo Fisher Scientific Inc.) supplemented with 10% FBS, 100 IU/ml of penicillin and 100 μg/ml of streptomycin in an incubator. Imiquimod (IMQ; TLR7 agonist) and CpG-ODN (ODN 2395; TLR9 agonist) were obtained from InvivoGen (San Diego, CA, USA), and hydroxychloroquine (HCQ; endosomal TLRs inhibitor) was obtained from Sigma Aldrich Co. (St. Louis, MO, USA).

Example 1

Confirmation of Cytotoxicity and TLR7/TLR7 Inhibitory Effect of Novel Compounds RAW264.7 cells were incubated along with 1, 10 or 50 μM of a compound. After 24 hours, MTT (3-(4,5-dimethylthiazol-2-yl)-2,5-diphenyltetrazolium bromide) assay and enzyme-linked immunosorbent assay (ELISA) were sequentially performed.

Figure 7B:
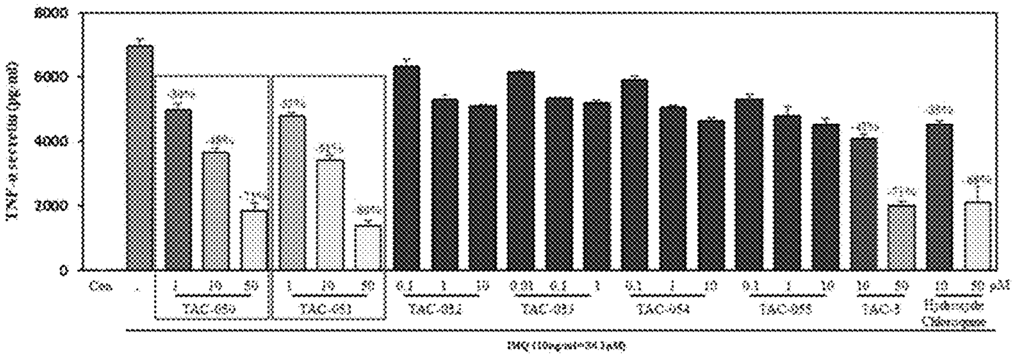
Figure 7C:
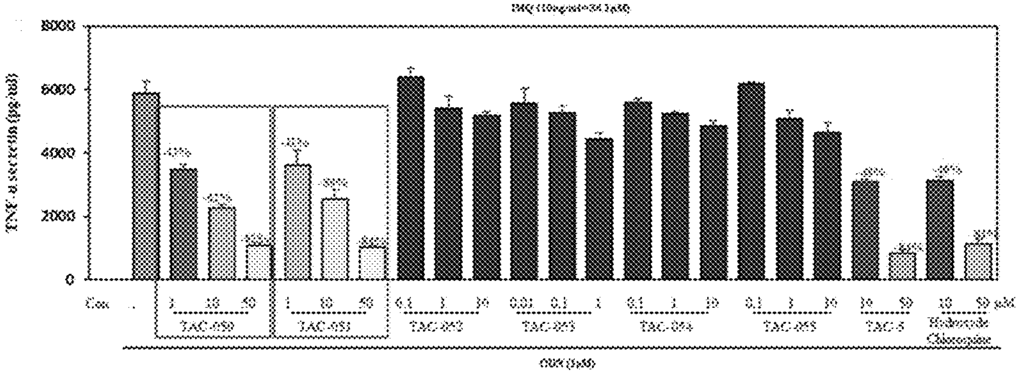

At concentrations of 1, 10 and 50 μM, TAC5-052, TAC5-053, TAC5-054, and TAC5-055 were cytotoxic, and TAC5-050 and TAC5-051 were non-cytotoxic (FIG. 7A). In addition, TAC5-050 and TAC5-051 inhibited the secretion of TLR7- or TLR9-induced TNF-α in a dose-dependent manner in the presence of IMQ or ODN 2395 (FIGS. 7B and 7C).

Example 2

Measurement of $IC_{50}$ of TAC5-050 and TAC5-051

The median inhibitory concentration ($IC_{50}$ ; half inhibitory concentration, concentration that shows 50% inhibition) achieved by small molecule compounds was determined. ODN 2395 was used as a ligand to activate TLR9 and IMQ was used to induce TLR7 activity. The inhibitory effects of TAC5-050 and TAC5-051 against TLR9 or TLR7 were determined. HCQ, which is known to inhibit endosomal TLRs, was used as a control group. Since the median inhibitory concentration was expected to range from 50 and 20 μM, the concentration range was set to decrease by half from the high concentration (50 μM) to the low concentration (20 μM).

Figure 8:
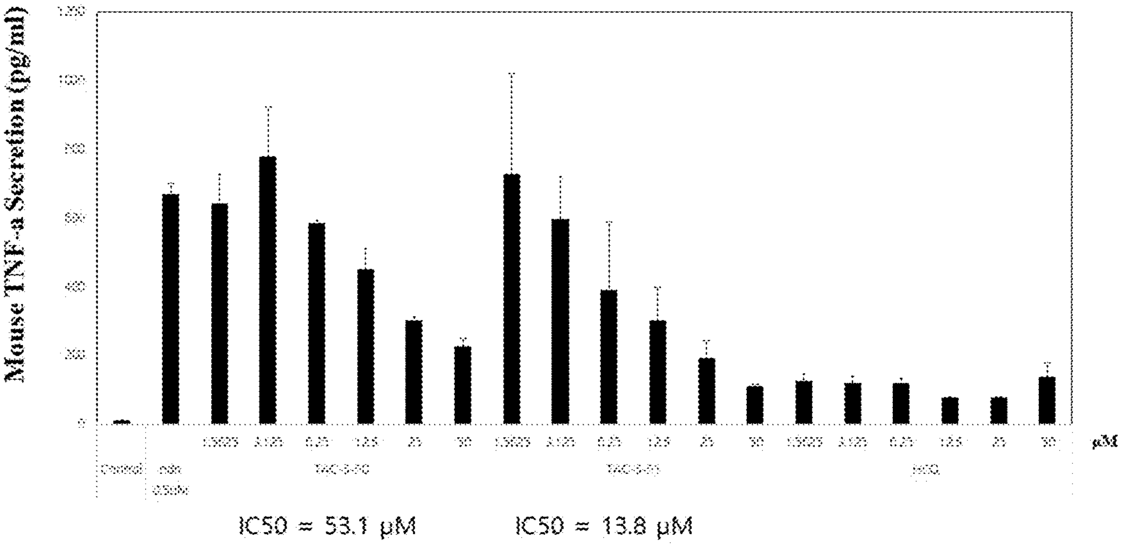
FIG. 8 shows the $IC_{50}$ of TAC5-050 and TAC5-051 for TLR9.
Figure 9:
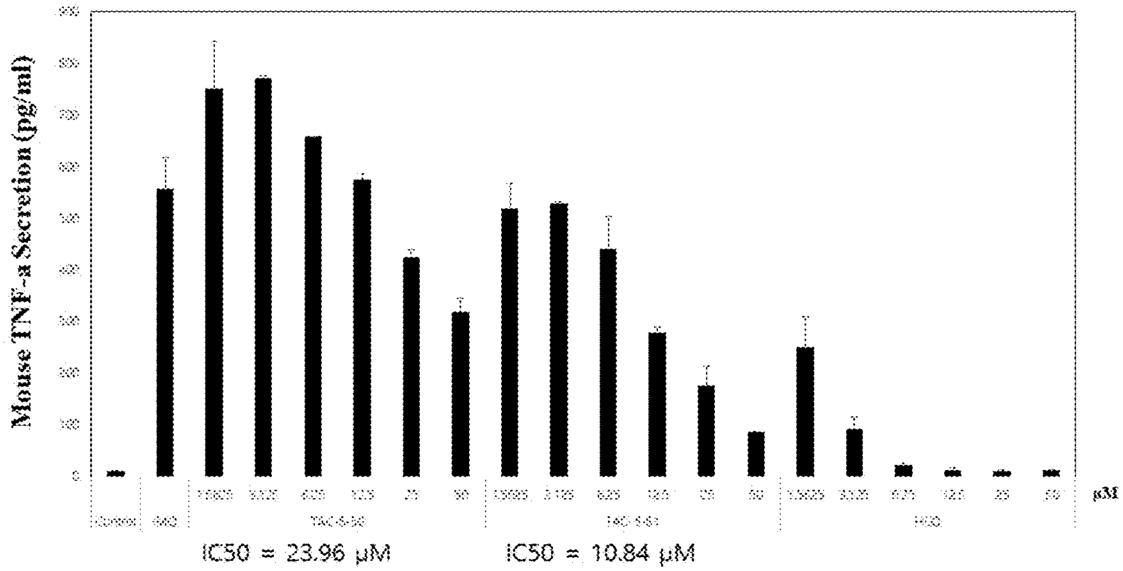
FIG. 9 shows the $IC_{50}$ of TAC5-050 and TAC5-051 for TLR7.

RAW264.7 cells ($2\times10^4$ cells/well) were treated with small molecule compounds and HCQ for 1 hour (0.25% DMSO), incubated and then treated with ODN 2395 (0.5 μM) or IMQ (1 μg/ml) for 4 hours. Then, the ELISA for detecting mTNF-α was performed in accordance with the following protocol:

1. Transfer samples from 96 well cell culture plate to elisa coated plate) and incubate for 2 h
2. Treat detection antibody and incubate for 1 h
3. Treat HRP and incubate for 30 min
4. Treat TMB and read the samples by using micro-plate reader machine The result of measurement showed that the $IC_{50}$ of TAC5-050 and TAC5-051 for TLR9 was 53.1 μM and 13.8 μM, respectively (FIG. 8), and the $IC_{50}$ of TAC5-050 and TAC5-051 for TLR7 was 23.96 μM and 10.84 μM, respectively (FIG. 9), which indicates that TAC5-050 and TAC5-051 inhibited TLR7 or TLR9 more effectively than the control group, HCQ.

INDUSTRIAL APPLICABILITY

The novel compounds according to the present invention block the secretion of TNF-α induced by IMQ (TLR7 agonist) or CpG-ODN (TLR9 agonist), and inhibit the production of inflammatory cytokines, in particular, systemic lupus erythematosus and psoriasis, thus being useful for the prevention or treatment of TLR7/9-related autoimmune diseases and inflammatory diseases.

Although specific configurations of the present invention have been described in detail, those skilled in the art will appreciate that this description is provided to set forth preferred embodiments for illustrative purposes and should not be construed as limiting the scope of the present invention. Therefore, the substantial scope of the present invention is defined by the accompanying claims and equivalents thereto.

The invention claimed is:

1. A compound selected from the group consisting of compounds of Formulas 1-2, 1-4, and 1-5, or a pharmaceutically acceptable salt thereof:

[Formula 1-2]

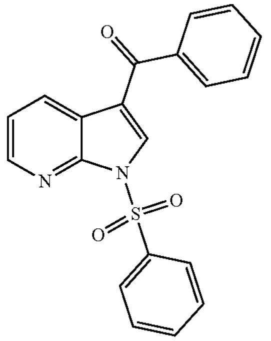

-continued

[Formula 1-4]

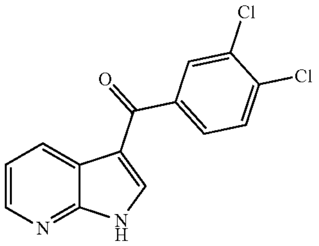

[Formula 1-5]

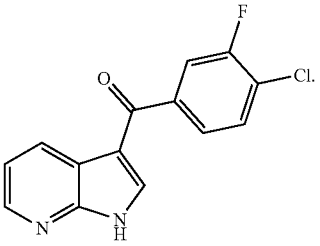

2. A method of preparing a compound of Formula 1-1, the method comprising reacting a solution of phenyl(1H-pyrrolo [2,3-b]pyridin-3-yl) methanone in N,N-dimethylformamide (DMF) with sodium hydride and 2-iodopropane to synthesize (1-isopropyl-1H-pyrrolo[2,3-b]pyridin-3-yl)-phenyl-methanone:

[Formula 1-1]

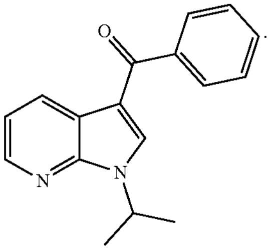

3. A method of preparing a compound of Formula 1-2, the method comprising reacting a solution of phenyl(1H-pyrrolo [2,3-b]pyridin-3-yl) methanone in N,N-dimethylformamide (DMF) with sodium hydride and benzenesulfonyl chloride to synthesize (1-benzylsulfonyl-1H-pyrrolo [2,3-b]pyridin-3-yl)-phenyl-methanone:

[Formula 1-2]

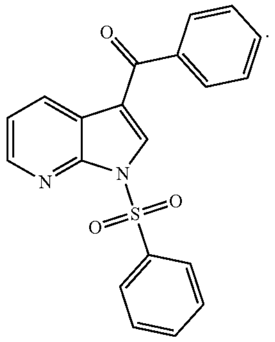

4. A pharmaceutical composition comprising the compound or a pharmaceutically acceptable salt thereof according to claim 1, and a pharmaceutically acceptable carrier.

5. A method for treating an autoimmune disease or an inflammatory disease in a subject in need thereof, comprising administering to the subject an effective amount of a composition comprising the compound or a pharmaceutically acceptable salt thereof according to claim 1.

6. The method of claim 5, wherein the autoimmune disease or inflammatory disease is selected from the group consisting of psoriasis, systemic lupus erythematosus (SLE), skin rash, photosensitivity, arthritis, oral ulcer, nephritis, hemocytopenia, vasculitis, serositis, inflammatory bowel disease (IBD), diabetes, multiple sclerosis, skin sclerosis, pemphigus, atopic dermatitis, urethritis, cystitis, arteriosclerosis, allergic diseases, rhinitis, asthma, acute pain, chronic pain, periodontitis, gingivitis, gout, myocardial infarction, congestive heart failure, high blood pressure, angina pectoris, gastric ulcer, cerebral infarction, Down's syndrome, obesity, dementia, depression, schizophrenia, tuberculosis, sleep disorders, sepsis, burns, pancreatitis, Parkinson's disease, stroke, and a combination thereof.

* * * * *